US012029561B2

(12) United States Patent
Lundquist et al.

(10) Patent No.: US 12,029,561 B2
(45) Date of Patent: Jul. 9, 2024

(54) PROCOAGULANT FACTORS SUITABLE FOR SUBSEQUENT AUTOLOGOUS USE

(71) Applicant: REAPPLIX APS, Birkerød (DK)

(72) Inventors: Rasmus Lundquist, Brønshøj (DK); Niels Erik Holm, Birkerød (DK)

(73) Assignee: REAPPLIX APS, Birkerød (DK)

( * ) Notice: Subject to any disclaimer, the term of this patent is extended or adjusted under 35 U.S.C. 154(b) by 291 days.

(21) Appl. No.: 16/068,514

(22) PCT Filed: Jan. 6, 2017

(86) PCT No.: PCT/EP2017/050263
§ 371 (c)(1),
(2) Date: Jul. 6, 2018

(87) PCT Pub. No.: WO2017/118729
PCT Pub. Date: Jul. 13, 2017

(65) Prior Publication Data
US 2019/0000367 A1    Jan. 3, 2019

(30) Foreign Application Priority Data

Jan. 6, 2016 (EP) .................................. 16150311
Jan. 14, 2016 (DK) ........................... PA 2016 70017

(51) Int. Cl.
*A61B 5/15* (2006.01)
*A61B 5/154* (2006.01)
(Continued)

(52) U.S. Cl.
CPC .... *A61B 5/150755* (2013.01); *A61B 5/15003* (2013.01); *A61B 5/150099* (2013.01);
(Continued)

(58) Field of Classification Search
CPC ........ A61B 5/150755; A61B 5/150099; A61B 5/150343; A61B 5/154; A61B 5/1438;
(Continued)

(56) References Cited

U.S. PATENT DOCUMENTS 2,460,641 A    2/1949 Kleiner
3,814,248 A    6/1974 Lawhead
(Continued)

FOREIGN PATENT DOCUMENTS

CN    101185574 A    5/2008
CN    201135444 Y    10/2008
(Continued)

OTHER PUBLICATIONS

Japanese First Search Report dated Aug. 5, 2019 from corresponding Japanese Patent Application No. 2017800072374, 2 pages.
(Continued)

*Primary Examiner* — Sarah Al Hashimi
*Assistant Examiner* — Meagan Ngo
(74) *Attorney, Agent, or Firm* — Ruggiero McAllister & McMahon LLC

(57) ABSTRACT

Provided is a blood collection unit suitable for accelerated blood coagulation of whole blood for subsequent autologous or allogeneic use. The blood collection unit includes an inside surface that an activation site accelerating coagulation by having a high roughness. Further provided is a blood collection unit including an inside surface that has an activation site having a high roughness area, and an interior of the blood collection unit has been prepared with a pressure of no more than 255 mBar, and preferably a pressure of no more than 130 mBar.

14 Claims, 8 Drawing Sheets

(51) Int. Cl.
  *B01L 3/00* (2006.01)
  *G01N 33/49* (2006.01)
(52) U.S. Cl.
  CPC .. *A61B 5/150274* (2013.01); *A61B 5/150351* (2013.01); *A61B 5/150389* (2013.01); *A61B 5/150473* (2013.01); *A61B 5/154* (2013.01); *B01L 3/5082* (2013.01); *G01N 33/491* (2013.01); *A61B 5/1438* (2013.01); *A61B 5/150503* (2013.01); *B01L 3/505* (2013.01)
(58) Field of Classification Search
  CPC ... A61B 5/1405; A61F 5/150343; B01L 3/50; A61J 1/05
  See application file for complete search history.

(56) References Cited

U.S. PATENT DOCUMENTS

| | | | |
|---|---|---|---|
| 5,326,535 | A | 7/1994 | Vogler et al. |
| 5,344,611 | A * | 9/1994 | Vogler ............... B01L 3/5082 422/547 |
| 5,533,518 | A | 7/1996 | Vogler |
| 5,634,474 | A * | 6/1997 | Grippi ............... G01N 33/491 600/576 |
| 5,733,545 | A | 3/1998 | Hood, III |
| 6,040,493 | A | 3/2000 | Cooke et al. |
| 6,686,204 | B2 | 2/2004 | Dubrowny et al. |
| 8,137,663 | B2 | 3/2012 | Groene et al. |
| 8,158,412 | B2 | 4/2012 | Porat et al. |
| 8,168,230 | B2 | 5/2012 | Evangelista |
| 8,268,362 | B2 | 9/2012 | Braun et al. |
| 8,980,301 | B2 | 3/2015 | Lundquist et al. |
| 8,993,321 | B2 | 3/2015 | Suzuki et al. |
| 2001/0025154 | A1 | 9/2001 | Rapp |
| 2003/0045857 | A1 * | 3/2003 | Dubrowny ............. A61B 5/154 604/416 |
| 2004/0217046 | A1 | 11/2004 | Konrad |
| 2005/0023182 | A1 | 2/2005 | Shah |
| 2006/0140923 | A1 | 6/2006 | Evangelista |
| 2008/0089867 | A1 | 4/2008 | Fernandes et al. |
| 2008/0199513 | A1 | 8/2008 | Bertta et al. |
| 2009/0162587 | A1 | 6/2009 | Wilkinson et al. |
| 2010/0222253 | A1 | 9/2010 | Roedersheimer |
| 2013/0081960 | A1 | 4/2013 | Schott |
| 2015/0351676 | A1 * | 12/2015 | Faurie ............... A61B 5/150305 600/583 |
| 2020/0093646 | A1 | 3/2020 | Locke et al. |

FOREIGN PATENT DOCUMENTS

| | | |
|---|---|---|
| CN | 101932386 A | 12/2010 |
| CN | 104799869 A | 7/2015 |
| EP | 0 193 279 A2 | 9/1986 |
| EP | 0 629 445 A2 | 12/1994 |
| EP | 0 740 155 A1 | 10/1995 |
| EP | 0 984 279 B1 | 3/2003 |
| EP | 1 637 145 A1 | 3/2006 |
| EP | 2 334 307 B1 | 10/2012 |
| JP | 1-313040 H | 12/1989 |
| JP | 6-197887 A | 7/1994 |
| JP | H07-35743 A | 2/1995 |
| JP | H07-255821 A | 10/1995 |
| JP | H08165245 A | 6/1996 |
| JP | H09-299357 A | 11/1997 |
| JP | H11-318868 A | 11/1999 |
| JP | 2001508807 A | 7/2001 |
| JP | 2002-333443 A | 11/2002 |
| JP | 2003-325485 A | 11/2003 |
| JP | 2004521938 A | 7/2004 |
| JP | 2006-514018 A | 4/2006 |
| JP | 2007-167124 A | 7/2007 |
| JP | 2008-295705 A | 12/2008 |
| JP | 2011-179913 A | 9/2011 |
| WO | 0132289 A1 | 5/2001 |
| WO | 02081007 A2 | 10/2002 |
| WO | 2004103440 A1 | 12/2004 |
| WO | 2007021344 A1 | 2/2007 |
| WO | 2009/117129 A2 | 9/2009 |
| WO | 2022/084478 A1 | 4/2022 |

OTHER PUBLICATIONS

Written Opinion of the International Searching Authority dated Feb. 27, 2017 from corresponding International Patent Application No. PCT/EP2017/050263, 9 pages.

International Search Report dated May 12, 2017 from corresponding International Patent Application No. PCT/EP2017/050263, 6 pages.

Written Opinion of the International Preliminary Examining Authority dated Dec. 4, 2017 from corresponding International Patent Application No. PCT/EP2017/050263, 10 pages.

International Preliminary Report on Patentability dated Mar. 16, 2018 from corresponding International Patent Application No. PCT/EP2017/050263, 18 pages.

"BD Vacutainer Evacuated Blood Collection System", Nov. 2010 (Nov. 2010), XP055262560, Retrieved from the Internet: URL:http://www.cliawaived.com/web/items/pdf/BD_367871_Blood_collection_insert~2911file1.pdf[retrieved on Apr. 4, 2016].

Bush et al., "The Evolution of Evacuated Blood Collection Tubes"; Lab Notes, a Newsletter from BD Diagnostics Preanalytical Systems, vol. 19, No. 1, 2009, 7 pages.

Fleisher et al., Use of Evacuated Collection Tubes for Routine Determination of Arterial Blood Gases and pH, Clinical Chemistry, vol. 17, No. 7, 1971, 7 pages.

Murayama, Makio, Ex Vivo Human Platelet Aggregation Induced by Decompression During Reduced Barometric Pressure, Hydrostatic, and Hydrodynamic (Bernoulli) Effect, 10 pages.

Japanese Notification of Reasons for Rejection dated Sep. 23, 2020 corresponding Japanese Patent Application No. 2018-535897, 11 pages.

Nilsson, Martin A. et al; "A novel and inexpensive technique for creating superhydrophobic surfaces using Teflon and sandpaper"; Journal of Physics D: Applied Physics, 43 (2010) 045301 (5 pp).

Balbino et al.; "Mechanisms Involved in Healing: a Review", Brazilian Journal of Pharmaceutical Sciences, vol. 41, No. 1, Jan./Mar. 2005, 46 pages.

Thermo Scientific; "Convert between times gravity (xg) and centrifuge rotor speed (RPM)", Thermo Scientific, Tech Tip #40, TR040.1, 1 page, 2009.

ThermoFisher. Blood fractionation protocol for collection of white blood cells. Thermo Fisher Scientific. 2002; 1-5.

Laurens, et al.; "Fibrin structure and wound healing", J. Thromb Haemost, 2006, 4: 932-939.

Jay et al., "How Anticoagulants Work", Techniques in Regional Anesthesia and Pain Management, 10, 2006, pp. 30-39.

Dohan, David M. et al., "Platelet-rich fibrin (PRF): A second generation platelet concentrate. Part I: Technological concepts and evolution", Oral Surg Oral Med Oral Pathol Oral Radiol Endod, 2006, pp. E37-E 44, vol. 101, No. 3.

Dohan, David M et al., "Platelet-rich fibrin (PRF): A second generation platelet concentrate. Part II: Platelet-related biologic features", Oral Surg Oral Med Oral Pathol Oral Radiol Endod, 2006, pp. E45-E 50, vol. 101, No. 3.

Dohan, David M. et al., "Platelet-rich fibrin (PRF): A second generation platelet concentrate. Part III: Leucocyte activation: A new feature for platelets concentrates?", Oral Surg Oral Med Oral Pathol Oral Radiol Endod, 2006, pp. E51-E 55, vol. 101, No. 3.

Choukroun, Joseph et al., "Platelet-rich fibrin (PRF): A second-generation platelet concentrate. Part IV: Clinical effects on tissue healing", Oral Surg Oral Med Oral Pathol Oral Radiol Endod, 2006, pp E56-E60, vol. 101, No. 3.

Choukroun, Joseph et al., "Platelet-rich fibrin (PRF): A second-generation platelet concentrate. Part V: Histologic evaluations of PRF effects on bone allograft maturation in sinus lift", Oral Surg Oral Med Oral Pathol Oral Radiol Endod, 2006, pp. 299-303, vol. 101, No. 3.

(56) References Cited

OTHER PUBLICATIONS

Sutton, Don W. et al., Cell Separation in the Buffy Coat, Biorheology, 1988, pp. 663-673, vol. 25, No. 4.

Kalus, M. et al., "Human Buffy Coat in Three-Dimensional Matrix Tissue Cultures and Monolayers", Pathologia et Microbiologia, 1968, pp. 353-364, vol. 31, No. 6.

Everts, P. A. M. et al., "Differences in platelet growth factor release and leucocyte kinetics during autologous platelet gel formation", Transfusion Medicine, 2006, pp. 363-368, vol. 16, No. 5.

Raja V., Sunitha et al., "Platelet-rich fibrin: Evolution of a second-generation platelet concentrate", Indian J Dent Res., 2008, pp. 42-46, vol. 19, No. 1.

Diss, Antoine et al., "Osteotome sinus floor elevation using Choukroun's platelet-rich fibrin as grafting material: a 1-year prospective pilot study with microthreaded implants", Oral Surg Oral Med Oral Pathol Oral Radiol Endod, 2008, pp. 572-579, vol. 105, No. 5.

Dohan-Ehrenfest et al., "Three-Dimensional Architecture and Cell Compositions of a Choukroun's Platelet-Rich Fibrin Clot and Membrane", J. Periodontology 81: 546-555 (2010).

Hattori, Akira: "A Simple Micromethod of Preparing Peripheral Leukocytes and Platelets for Electron Microscopy", Arch. Histol. Jap. 32 (4) : 307-313 (1970).

Nunes et al., "Micro-Buffy Coats of Whole Blood: A Method for the Electron Microscopic Study of Mononuclear Cells", Stain Technology, vol. 54, No. 5: 257-260 (1979).

Lundquist et al.; Bioactivity and stability of endogenous fibrogenic factors in platelet-rich fibrin, Wound Repair and Regeneration 16 : 356-363, May 1, 2008.

Clark, Richard AF; "Fibrin Sealant in Wound Repair: A Systematic Survey of the Literature", Expert Opinion on Investigational Drugs, 9:10, 2371-2391, DOI: 10.1517/13543784.9.10.2371.

De Iaco et al.; "Fibrin sealant in laparoscopic adhesion prevention in the rabbit uterine horn model", Fertility and Sterility, vol. 62, No. 2, Aug. 1994, pp. 400-404.

Lundquist et al.; "Characteristics of an autologous leukocyte and platelet-rich fibrin patch intended for the treatment of recalcitrant wounds", Wound Rep Reg, Wound Healing Society, 2013, 21, pp. 66-76.

Thomsen et al.; "The phagocytic fitness of leucopatches may impact the healing of chronic wounds", British Society for Immunology, 2016, Clinical and Experimental Immunology, 10 pages.

Cadamuro, Janne et al. "In-vitro hemolysis and its financial impact using different blood collection systems." LaboratoriumsMedizin 40 (2015): 49-55.

Martineau et al.; "Effects of calcium and thrombin on growth factor release from platelet concentrates: Kinetics and regulation of endothelial cell proliferation"; Biomaterials, 25, 2004, pp. 4488-4502.

\* cited by examiner

PROCOAGULANT FACTORS SUITABLE FOR SUBSEQUENT AUTOLOGOUS USE

BACKGROUND OF THE DISCLOSURE

1. Field of the Disclosure

The present invention relates to a method, apparatus and kit suitable for accelerating blood coagulation in blood without requiring the use of additives.

2. Description of Related Art

After drawing blood from patients, coagulation of the fibrin in blood is desirable in some circumstances, such as for analysis of blood or for preparation of platelets and leucocyte-rich fibrin patch. In these circumstances, it is desirable to complete fibrin polymerisation as rapidly as possible to save processing time. Furthermore, the coagulation speed differs from patient to patient, and certain patients have blood which coagulates slowly, such as patients on anticoagulant therapy drugs like Xarelto®, Warfarin or alike. For these patients with slow coagulation speed, the speed may be so slow as to impede autologous treatment and/or reduce the quality of blood clot and serum substantially thus reducing treatment quality for potentially notably vulnerable patients and increasing the risk of e.g. needing perpetual treatment.

For these reasons, there is a need for blood coagulation accelerators and furthermore for blood collection equipment and methods which provide an enhanced rate of blood coagulation without leaving any soluble or particulate material in the serum layer or in the clot after centrifugation thus avoiding potential interference with clinical tests or contaminations when used autologous, such as for blood testing/analysis and for production of LeucoPatch® as disclosed in EP2334307B1.

US 2009/0162587 describes a vacuum blood collection container useful for making a full blood draw from a patient, where a full blood draw is 3.5 ml of blood. It describes that for example to achieve a full blood draw for a vacuum tube of 7 ml, the container would need an internal pressure of between 133 mBar and 400 mBar.

Known methods for accelerating and activating coagulation include exposure to diatomaceous earth and particles of inorganic silicates, and bio-chemicals such as ellagic acid and thromboplastin. US 2003/0045857 discloses a coating for a blood collection container having a compound of either thrombin, heparinase and/or fibrinogen combined with diatomaceous earth combining different procoagulant factors to create an effective procoagulant environment. A problem with particulate activators is that finely divided particles may not all adhere to the container inner wall and may thus contaminate the serum layer and interfere with certain blood uses. On the other hand, soluble biochemical activators can be disadvantageous because these cannot be separated easily from either the serum or blood clot and leave the blood non-autologous. For specialised autologous applications, it is unacceptable to have either soluble activators or particulates in the cell mass of a blood clot.

In one line of commercial blood collection tubes, for example a coating of silicate particles in polyvinylpyrrolidone (PVP, a water-soluble polymer) is affixed to the inside of the tube. When blood enters the tube, the PVP dissolves and silicate particles are released to initiate clotting. This constitutes a contamination of said blood for autologous uses.

EP0740155A1 discloses serum tubes coated with material that activates the coagulation, but said coating material may not adhere firmly to the serum tube surfaces and may therefore be carried forward into subsequent process steps. This constitutes a contamination of said blood sample which is as problematic as the retention of chemical additives mentioned above.

EP0984279B1 discloses a method for accelerating blood coagulation relying on the biochemical additives thrombin and/or batroxobin. The resultant coagulated blood product may be useful for certain clinical tests, but the additives make it unsatisfactory for other uses such as autologous treatments.

EP 0 629 445 A2 discloses an evacuated blood collection assembly including a plastic container having a plasma-treated inside wall surface and an open end covered by a puncturable septum.

U.S. Pat. No. 5,533,518 A discloses blood collection assembly including a tube, which may be evacuated.

U.S. Pat. No. 5,326,535 A discloses a blood collection container is coated on its inside wall with a unitarily immobilized clotting activator. The activator may be applied to the surface by an adhesive or by rendering the inside wall surface sticky with a solvent and partially absorbing the activator into the sticky surface.

The document "BD Vacutainer Evacuated Blood Collection System" (November 2010) retrieved from the Internet: URL:http://www.cliawaived.com/web/items/pdf/BD 367871 Blood collection insert "2911file1.13df discloses tubes, needles and holders used together as a system for the collection of venous blood.

SUMMARY OF THE DISCLOSURE

A first object of the invention is to solve the above-mentioned problems by providing a blood collection unit suitable for accelerated blood coagulation of whole blood for subsequent autologous or allogeneic use having an outer wall comprising a closed bottom end, an open top end, a side wall spanning between said ends, and a stopper for inserting in said open end to releasably seal said blood collection container, the stopper having a puncturable self-sealing septum (105) or valve, an inner volume at least partially bounded by an inside surface of said outer wall, and a procoagulant environment, wherein said inner volume is prepared with a pressure of no more than 100 mBar.

The unit could e.g. be a blood collection container. Alternatively, it could be a tube or a needle transporting the blood sample from a blood-filled cavity, such as a patient, to the blood collection container.

Thereby, blood coagulation is accelerated within the container thus speeding up medical procedures dependent on coagulation of blood absent of additives and contaminants which would make the blood unsuited for certain uses, such as blood testing/analysis and LeucoPatch®. A pure and uncontaminated coagulated autologous blood product is achieved from a blood sample significantly faster. When drawing blood without anticoagulant additive, such as when taking serum samples or blood for LeucoPatch® preparation, it is crucial to achieve fibrin coagulation as rapidly as possible, especially when the blood sample is taken form a patient on anticoagulant therapy drugs like Xarelto®, Warfarin or the like.

The roughness may be achieved by various methods. In one embodiment, it is achieved by abrasion, such as sanding. In this embodiment, it may be sanded by any grit sizes. Grits between 100 and 1,000 are useful, where grits such as between 300 and 600 may be convenient.

Alternatively, it may be achieved by sparking, milling, embossing or other ways that provide an uneven and/or jagged surface. In an embodiment, the roughness is achieved by applying the rough surface to the mould for casting the blood collection containers. In an embodiment of the invention, the surface might be provided by imprinting.

Roughness in the present context is related to surface finish, surface texture, or surface topography. By roughness is meant that the surface is non-smooth. This means, roughness is height deviations in the direction of the normal vector of a real surface from its ideal form. By an ideal form is meant a smooth surface in the present context. If the height deviations are large, the surface is said to be rough, whereas small height deviations correspond to a smooth surface. A rough surface may be said to be uneven or irregular.

By having a rough surface, the total surface area is larger compared to a corresponding smooth surface since inevitably, the height deviations introduce additional area. Roughness may be quantified using various measures. Historically, the roughness average $R_a$ has often been employed being the arithmetic average of the absolute deviations measured from a common reference. Another measure is the root mean square of the roughness average $R_{RMS}$ being the root mean square, or standard deviation, of the roughness average. From the calculation of $R_{RMS}$, e.g. a single large deviation within the non-smooth surface will affect $R_{RMS}$ more than $R_a$, since it weighs such deviations more heavily.

When quantifying roughness within the present context, the root mean square of the roughness average $R_{RMS}$ is employed.

The container used may be produced in various materials. Preferably, it is produced in a material such as PET, nylon type polymers and other, preferably hydrophilic polymers. However, the invention works well with the hydrophobic polymers as well. Surprisingly, it has been found that the rough surface helps activate coagulation/speed up coagulation of the blood. It is known in the art that glass has a procoagulant effect on blood which has been attributed to it being extremely hydrophilic. Further, it is established in the art that plastics do not activate coagulation/speed up coagulation which has been attributed to their comparatively hydrophobic surfaces. However, with the increase of surface area and/or uneven/sharp edges, this has been overcome.

In an embodiment, the activation site is located at the bottom of the blood collection container. By providing the activation site at the bottom of the blood collection container, it allows the blood to impact/splash against the activation site during the very initial blood draw. Further, the blood will be pressed against the activation site during centrifugation, enhancing the effect hereof.

In an embodiment, the activation site is located on the side wall of the blood collection container.

In an embodiment, the activation site is located on both the sidewall and at the bottom. In an embodiment, the activation site covers the entire inside surface of the blood collection container substantially. In an embodiment, the activation side covers the entire inside surface of the blood collection container.

In an embodiment, the blood collection container comprises an insert in its inner volume, where the activation site is located on the insert.

In an embodiment, the insert comprises a float and a mesh. In this embodiment, the float is adapted to lift the insert to the top of the container at some time during or after centrifugation. Lifting the float may depend on outside forces such as a device pressing against the outside of the container until a predefined pattern has been met, such as a sufficiently translucent/opaque optical reading, when the blood sample is lit through. The mesh is adapted to collect at least the fibrin fraction of the blood during coagulation.

In an embodiment comprising an insert with a float and a mesh, the activation site is located on the upper surface of the float. Thereby, a surface is treated which is easy to access compared to the sidewalls and bottom walls during production of the blood collection container as it can be treated prior to being inserted into the blood collection container. Further, this also allows the blood to press against the activation site during centrifugation and allows the blood to impact/splash against it during the very initial blood draw.

In an embodiment, the activation site has a roughness of at least 0.012 µm, at least 0.025 µm, at least 0.05 µm, at least 0.1 µm, at least 0.2 µm or at least 0.4 µm.

In an embodiment, the activation site is hydrophobic.

In an embodiment, the inside surface is hydrophobic.

In an embodiment, the blood collection unit is made of a hydrophobic material.

By the activation site, the inside surface, or the blood collection unit being hydrophobic or being made from a hydrophobic material is meant that water is repelled from the surface. Water is a component of whole blood, especially of the blood plasma, thus making it relevant to consider hydrophobicity. Physically, hydrophobicity may be described and quantified using the contact angle between a water droplet and the possible hydrophobic surface. The contact angle for a hydrophobic surface may be larger than 90° measured where the liquid vapour interface meets the possible hydrophobic surface. The contact angle is the angle between a tangent at a liquid vapour surface triple point and measured towards the droplet. Thus, for a highly hydrophobic material, the droplet is almost spherical, causing a large contact angle, theoretically approaching 180°. Thus, the activation site, the inside surface, or the entire blood collection unit repels a majority, i.e. the water contents, of the whole blood. By repelling a majority of the whole blood, the activation site is kept clean thereby maintaining procoagulant properties. If the surface is not hydrophobic, clots may arise within the activation site thereby preventing further coagulating processes within the activation site.

In an embodiment, the inside surface has not been corona-treated. Corona treatment, or plasma treatment, is known to increase the surface area and to make the surface less hydrophobic and is known in the art to activate coagulation. By avoiding corona treatment, the activation of the coagulation process relies mainly on the high roughness. The combination of high roughness and corona-treated surface will result in improved activation, but the effect of corona treatment may decrease with time.

In an embodiment, the blood collection unit is a tube or double-ended needle. The tube and the double-ended needle may be connected. Thereby, whole blood may be drawn from a first needle end of the double-ended needle, e.g. connected to a patient, to a second needle end of the double-ended needle. The coagulation processes may be initiated during the transport of the whole blood through an inner volume of the tube.

In an embodiment, the blood collection unit is a blood collection container, wherein the outer wall comprises a closed bottom end, an open top end, a side wall spanning between said ends and a stopper for inserting in said open end to releasably seal said blood collection container. The stopper has a puncturable self-sealing septum or valve.

In an embodiment, the procoagulant environment further comprises that the inner volume has been prepared with a pressure of no more than 255 mBar. In an embodiment, the inner volume is prepared with a pressure of no more than 200 mBar. In an embodiment, the inner volume is prepared with a pressure of no more than 130 mBar.

In an embodiment, the inner volume is prepared with a high vacuum. This high vacuum could be a pressure of no more than e.g. 100 mBar, or no more than 200 mBar, or no more than 255 mBar.

In an embodiment, the activation site as a procoagulant is combined with a high vacuum in the blood collection container prior to blood draw which also serves as a procoagulant. This combination serves to further decrease the total coagulation time. The initial high vacuum will draw blood into the container faster than vacuums used merely to facilitate the draw, such as the vacuums of Vacutainer® of about 300 mBar. The blood entering the blood collection enters with the highest speed initially and as the blood fills the container, the pressure in the container will be slowly normalised thus making the blood enter progressively slower. The initial high speed of the blood in a container with above conventional vacuum likely produces mechanical agitation of the blood which activates the blood coagulation cascade.

Such high speed could also be obtained by other means than a container with a vacuum, e.g. by initially drawing the blood into a syringe and then applying pressure on the syringe piston, when blood is filled into the device. Generally, the blood just needs to be delivered, at least initially, to the interior of the container with a high speed. This can e.g. be obtained with other means, e.g. where there is a pressure difference between the source and the destination of the blood.

Where the activation site is hit with an initial drop of blood, the effect is even further increased as the blood is exposed to the uneven surface with a greater force.

In an alternative embodiment, there is provided a blood collection container suitable for accelerated blood coagulation for subsequent autologous or allogeneic use of whole blood having an outer wall comprising a closed bottom end, an open top end, a side wall spanning between said ends, and a stopper for inserting in said open end to releasably seal said blood collection container, the stopper having a puncturable self-sealing septum or valve. Inside the container there is an inner volume bounded by an inside surface of said outer wall including said stopper. The blood collection container further comprises a procoagulant environment, wherein the procoagulant environment comprises said inner volume (101) being prepared with a pressure of no more than 255 mBar.

The inventive method comprising creating and maintaining a high vacuum environment inside the blood collection container has the effect of accelerating blood coagulation of a blood sample within said container thus speeding up medical procedures dependent on coagulation of blood absent of additives and contaminants which would make the blood unsuited for certain uses, such as blood testing/ analysis and LeucoPatch®.

Thereby, a pure and uncontaminated coagulated autologous blood product is achieved from a blood sample significantly faster than previously possible. When drawing blood without anticoagulant additive, such as when taking serum samples or blood for LeucoPatch® preparation, it is crucial to achieve fibrin coagulation as rapidly as possible, especially when the blood sample is taken form a patient on anticoagulant therapy drugs like Xarelto®, Warfarin, or alike.

Any container capable of holding a vacuum is suitable for use in the current invention. Most conveniently, a blood collection container, which is suitable for generating and maintaining the high vacuum of the current invention, is suitable.

In one embodiment, this is provided by a blood collection kit of parts comprising a blood collection container. Said blood collection container comprises a bottom wall, a side wall defining an open end, and a stopper in said open end, said stopper further comprising a puncturable self-sealing septum or valve, said elements defining an inner volume of said container. The blood collection container may be any container having a closed end and an open end, for example bottles, vials, flasks and the like. Any material or aggregate of materials capable of maintaining a high vacuum with at least a transitory durability and suitable for subsequent clinical use may be used in the blood collection container, including but not limited to glass, polyethylene terephthalate (PET) and/or polystyrene (PS).

In one embodiment of the invention, said blood collection container is at least transitorily vacuum-durable.

Having a vacuum-durable blood collection container allows the vacuum to better persist better over time which allows easier handling and more efficient production, such as allowing an industrially produced blood collection container to retain a vacuum during subsequent processing and transport.

In one embodiment of the invention, a tube from a blood container with anti-coagulated blood, for example a blood plastic bag and bag systems, may be directly connected to a vacuum device—preferably by a needle fitted on the tube.

In one embodiment of the invention, a part of the inner surface of said bottom wall and/or a part of the inner surface of said side wall of the blood collection container has been plasma treated. In another embodiment, the entire inner surface of the walls has been plasma-treated. Optionally, in either embodiment, the inside of said stopper may also be plasma-treated. Likewise, parts placed inside the container may also be plasma treated.

The plasma may be generated from any suitable process gas. A representative but not limiting list of suitable process gases includes nitrogen, ammonia, carbon dioxide, sulphur dioxide, air, and oxygen, wherein air and oxygen are preferred. The tube may be placed open end up between the electrodes of a conventional plasma generator equipped with a pressure gauge, a gas inbleed, and a vacuum connection. Suitable electrodes may be of any conducting material, although stainless steel and aluminum are preferred. The width and shape of the electrodes are not critical. Any suitable ionising plasma may be used, as for example a plasma generated by a corona discharge or a glow discharge. When a plasma is generated by a corona discharge, the plasma treatment is commonly referred to as corona treatment.

Likewise, atmospheric pressure plasma treatment or other technologies used for surface treatment include in-line atmospheric (air) plasma, flame plasma, and chemical plasma systems.

Alternatively or additionally, the insides may be abraded in any convenient way. The surface may be roughened by any conventional chemical or mechanical method, or during the tube-forming process. Most conveniently, the surface is merely rubbed with an abrasive, such as with sand or emery paper. No limitation is placed on the grit of the abrasive.

Plasma treating and/or abrading increases surface area and friction with the blood and is known in the art to activate coagulation. Combining the high vacuum with another coagulation activator useful for autologous use further increases coagulation speed, blood product quality, and time for post-treatment care.

In an embodiment of the current invention, the blood collection container having in its inner volume a high vacuum is inserted into a first container or first container means characterised in that it possesses at least transitory vacuum durability and furthermore, that it can be subjected to a sterilisation procedure and can retain at least transitory vacuum durability. The first container means may take any shape, preferably being a bag or sack, and may consist of any type of material or aggregate of types of material. A representative but not limiting list of materials would include plastics, cardboard, glass, aluminium and/or aluminium foil. Said first container means comprises at least one material affording it transitory vacuum durability and furthermore allows sterilisation of said first container means and its inner volume without degrading its vacuum durability to less than a transitory vacuum durability, preferred actual materials being dependent on sterilisation method. In a preferred embodiment of the invention, the first container means comprises at least polyethylene terephthalate (PET) or polystyrene (PS).

Insertion into a first container means improves the durability of the high vacuum inside the blood collection container since now, the pressure drop from the outside air to the blood collection container has to permeate two barriers. This improves industrial applicability in a cost-efficient way since the blood collection container does not have to be produced with specifications to maintain its high vacuum during handling or transport, but only during use.

In one embodiment of the invention, the first container means containing the blood collection container has been sterilised. Any method of sterilisation may be used, but typically the most convenient techniques include heat (or heat and pressure) sterilisation, chemical sterilisation, radiation sterilisation, or any combination thereof. In a preferred embodiment, gamma-ray sterilisation is utilised.

Sterilisation either before or after insertion into a first container means is performed to significantly reduce risk of contamination during clinical use of the blood collection container and so to fulfil regulatory and safety requirements.

Because the high vacuum imposes a higher pressure differential on the blood collection container of this invention when compared to blood collection containers of the art, contaminations are more likely to be introduced simply by power of diffusion through imperfections in its construction, materials and/or seams. By inserting the blood collection container into a first vacuumed container means and sterilising it inside this said first vacuumed container means, the likelihood of any partial depressurisation and its associated risk of contamination of the inside of the blood collection container is eliminated or reduced.

In one embodiment of the invention, sterilization of the first container means containing the blood collection container is followed by inserting the first container means containing the blood collection container into a second container means, characterised in that said second container maintains a vacuum substantially durably, said second container means is then emptied of air and sealed. Preferably, said second container means comprises at least one material enabling said second container means to maintain a vacuum substantially durably. Said second container means may consist of any type of material or aggregate of types of material, a representative but not limiting list of materials would include plastics, cardboard, glass and/or aluminium. In a preferred embodiment of the invention, the second container means comprises at least aluminium or aluminium foil.

Sterilising the blood collection container inside the first container means with limited vacuum durability, which is unfit for long-time storage, provides a transitory vacuum durability even through sterilisation. To increase vacuum durability, the first container means containing the blood collection container is inserted into a second container means chosen for substantial vacuum durability and handling durability.

This dual-sealing allows a blood collection container to be produced which meets regulatory and safety requirements while attaining and maintaining a substantially durable vacuum through transportation and storage in a way that meets economic and industrial specifications.

In an embodiment of the invention, the blood collection container is sterilised before insertion into the first container means.

With a sufficiently high quality blood collection container, said high quality pertaining to it being substantially vacuum durable after a sterilisation procedure, it may not be necessary to dual-seal it to achieve the desired sterility and vacuum durability. Sealing it once and doing so after sterilisation is then sufficient for handling and vacuum durability purposes.

The blood collection container may be prepared with a high vacuum at any convenient time prior to, or during blood draw. An inexhaustible list of times is during manufacture and at a time prior to drawing blood recognising the vacuum durability of the used blood collection container ensuring that at least a high vacuum remains when drawing blood. In an embodiment of the invention, it is important to expose the blood to the high vacuum during blood draw to stress the blood cells significantly and so to initiate and/or accelerate coagulation.

The high vacuum of the blood collection container may be prepared in any convenient way, such as by using a vacuum pump. Likewise, the vacuums of the first and second container means may be applied in any convenient way.

In one embodiment of the invention, the blood coagulation inside the first blood collection container is further accelerated by at least one coagulation-accelerating object inside of it which accelerates blood coagulation through this exposure. For example, it may expose the blood to one or more glass surfaces, glass having been known in the art for a long time to promote coagulation. Such objects may be one or more glass beads.

By exposing the blood to a further coagulating agent, the coagulation time can be further decreased thus ensuring the shortest possible process time and so increasing time for post-treatment care.

The blood may be drawn into the blood collection container by any means used in the art. In one embodiment of the invention, the blood collection kit of parts further comprises a double-ended needle for drawing blood from a patient into the first blood collection container comprising a first needle-end, a second needle-end, and an intermediate tube, said double-ended needle comprising an inner volume running the axial length of the double-ended needle possibly with a fixed low inner volume of the double-ended needle system compared to the volume in the blood collection chamber in order to limit the depressurisation of the blood collection container during use.

In one embodiment of the invention, a first needle-end of said double-ended needle first enters a convenient blood-filled cavity, typically of a patient and preferably a vein of said patient. After the first needle end has entered its designated blood-filled cavity, a second needle end punctures the puncturable septum of the blood collection container. Then, the vacuum inside the inner volume of the blood collection container draws the blood from the patient by way of a pressure differential.

In an embodiment, the double-ended needle comprises an inside procoagulant environment. Thereby, the blood coagulation may be activated already when passing through the tube. In an embodiment, the procoagulant environment in the double-ended needle comprises an activation site with a high roughness.

Alternatively, collected blood may be removed from a blood container and may even be divided into smaller volume samples, some of which can also be used for different purposes or stored for later use.

In one embodiment of the invention, the first needle end may enter a previously filled second blood container instead of directly entering a patient. This allows potentially easier handling of the blood as well as drawing blood once and using it multiple times thus decreasing the number of times the skin of the patient needs to be penetrated among other advantages.

In one embodiment of the invention, the inner volume contains components adapted to counteract anti-coagulants added to the blood, such as calcium, at a level sufficient to counteract the activity of the anti-coagulants.

In another embodiment of the invention, the double-ended needle may be a catheter inserted into the circulatory system of a patient.

In one embodiment of the invention, the inner volume defined by the inner surface of the double-ended needle is such that bringing it into fluid communication with the inner volume of the blood collection container retains the high vacuum in the interior of the blood collection container. Consequently, this builds a high vacuum in the inner volume of the double-ended needle.

Achieving this combined high vacuum requires a comparatively higher initial vacuum in the blood collection container as well as a controlled volume of the double-ended needle, both taken together ensuring a controlled depressurisation before exposure to the blood. However, the balance of these two may take any form. For example, creating an extremely high vacuum in a large blood collection container allows a comparatively larger double-ended needle and conversely, a double-ended needle with a small volume will allow a lower grade vacuum and/or a smaller blood collection container.

In one embodiment of the invention, the double-ended needle has a fixed low inner volume $V_r$ or $V_a$ so as to limit the depressurisation of the blood collection container during use. For example, with a double-ended needle volume of 10% of the blood collection container of 100 ml and a prepared initial vacuum of 99%, the combined volume being 110 ml would hold 11 ml of air or 90% vacuum. Thus, a low inner volume of the double-ended needle ensures that the vacuum exerts a comparatively greater effect on the blood sample thus speeding up the coagulation and so increasing time for post-treatment care.

Another method to increase the pressure difference is to draw the blood into a syringe initially and then apply pressure on the syringe piston when blood is filled into the device.

In another embodiment of the invention, the double-ended needle has a membrane or pressure valve to control the flow of blood after injecting the first needle end into typically a vein and before inserting the second needle end into a blood collection container. It is then for example the pressure differential of bringing the two inner volumes into fluid communication that breaks or opens the membrane or opens the valve.

In one embodiment of the invention, the double-ended needle further comprises coagulation accelerating objects in its inner volume. By exposing the blood to coagulation activating objects here, process time is further decreased.

In an embodiment of the invention, the blood collection container further comprises an activation site formed in the inside surface, the activation site having a high roughness.

In an embodiment of the invention, the activation site has a roughness of at least 0.012 µm.

In an embodiment of the invention, the activation site is hydrophobic.

In an embodiment of the invention, the inside surface is hydrophobic.

In an embodiment of the invention, the blood collection container is made of a hydrophobic material.

In the above, a vacuum container has been described, where one effect is the resulting high speed with which the blood is delivered to the container. Such high speed could also be obtained by other means than a container with a vacuum, e.g. by initially drawing the blood into a syringe and then applying pressure on the syringe piston, when blood is filled into the device. Generally, the blood just needs to be delivered, at least initially, to the interior of the container at high speed. This can be obtained with other means, where there is a pressure difference between the source container and the destination container of the blood.

BRIEF DESCRIPTION OF THE DRAWINGS

In the following, example embodiments are described according to the invention, where.

DETAILED DESCRIPTION OF THE DISCLOSURE

In the following, the invention is described in detail through embodiments thereof that should not be thought of as limiting to the scope of the invention.

Figure 1:
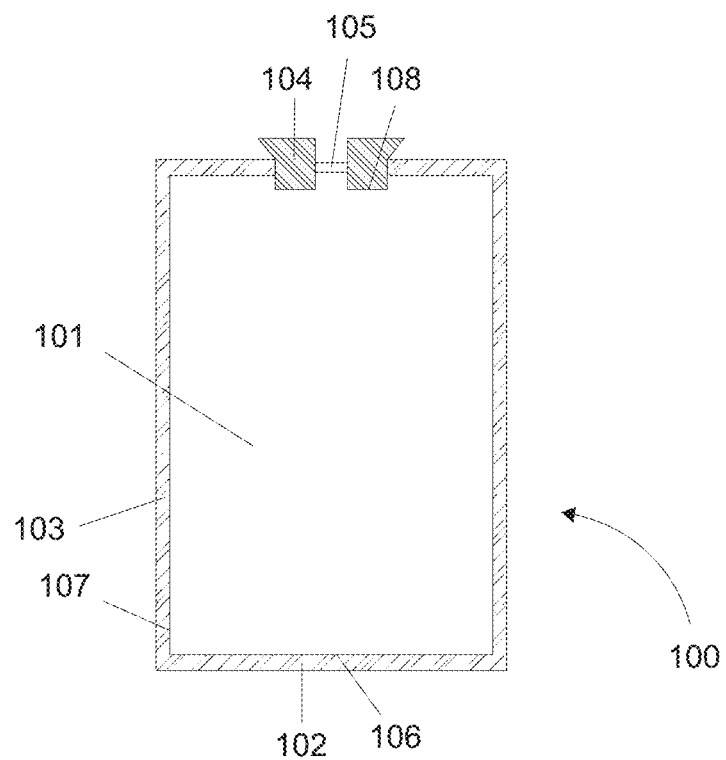
FIG. 1 is a side view of the evacuated blood collection container means according to the present invention.

FIG. 1 describes a side view of a blood collection container 100 comprising a bottom wall 102 and a side wall 103 forming a container with an open end and a closed end. A stopper 104 is fitted in said open end, said bottom wall 102, side wall 103 and stopper 104 enclosing an inner volume 101 of said blood collection container 100, said stopper comprising at least a mechanism for securely sealing said open end and maintaining a pressure differential, in a preferred embodiment making the blood collection container at least transitorily vacuum durable. Said stopper 104 further comprises a self-sealing puncturable septum 105 or a valve allowing the emptying of air from the inner volume 105 through any convenient method, such as a vacuum pump, said self-sealing puncturable septum 105 or valve further allowing the insertion of a needle or other tube-end without simultaneously allowing atmospheric air into the inner volume 101. This allows passage of blood through a needle into the blood collection container while maintaining a high vacuum in the inner volume 101.

Further depicted in FIG. 1 is an inner surface of said bottom wall 106, an inner surface of said side wall 107, and an inner surface of said stopper 108, said inner surfaces all facing and being in contact with said inner volume 101. These or some of these surfaces may be plasma-treated and/or abraded to accelerate coagulation speed further.

The blood collection container is prepared for use by inserting the stopper into its designated position in the open end of the blood collection container 100 and emptying the blood collection container of air through the self-sealing puncturable septum 105 or valve, said emptying of air further securing said stopper in its position by exerting a downward pressure due to the pressure differential over said stopper.

Figure 2:
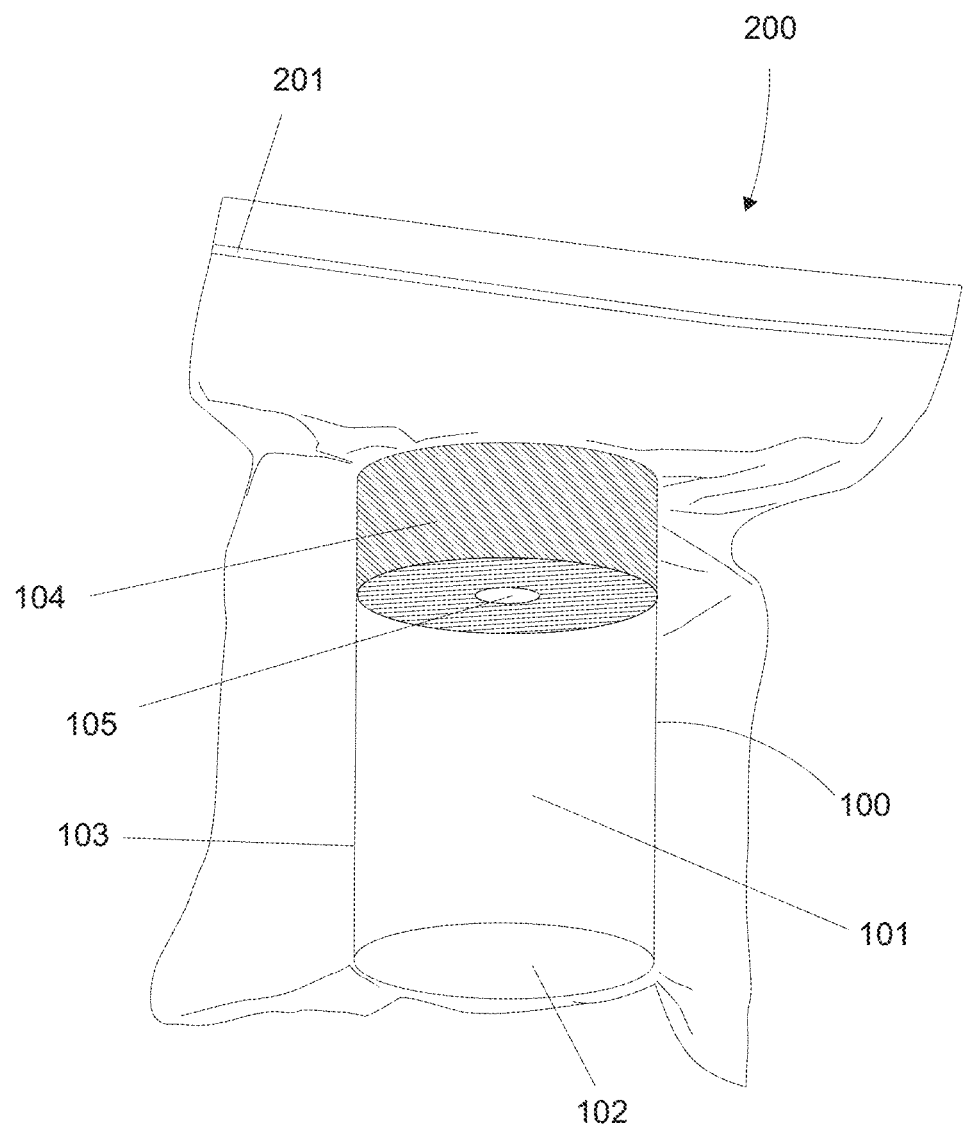
FIG. 2 is a view of the evacuated blood collection container means inserted into a first vacuum-sealed container means according to the present invention.

FIG. 2 is a side view of a blood collection container 100 inside a vacuum-sealed first container means 200, said first container means being at least transitorily vacuum durable, said blood collection container comprising a bottom wall 102, a side wall 103 defining a container with an open and a closed end, and a stopper 104 in said open end, said stopper further comprising a puncturable septum 105 or a valve for emptying the enclosed inner volume 101 of air thus creating a high vacuum, said puncturable septum or valve further allowing drawing blood into the blood collection container without simultaneously allowing atmospheric air into the inner volume 101.

The blood collection container is inserted into the first container means 200 which is emptied of air thus ensuring that it encloses said blood collection container tightly, whereupon said first container means is vacuum-sealed thus lowering the pressure differential over the bottom wall, side wall, and stopper of said blood collection container thus improving the effective vacuum durability of said blood collection container. Any convenient sealing method may be used and in one embodiment, when a convenient vacuum has been achieved inside the first container means, it is heat-sealed at the sealing line 201.

Figure 3:
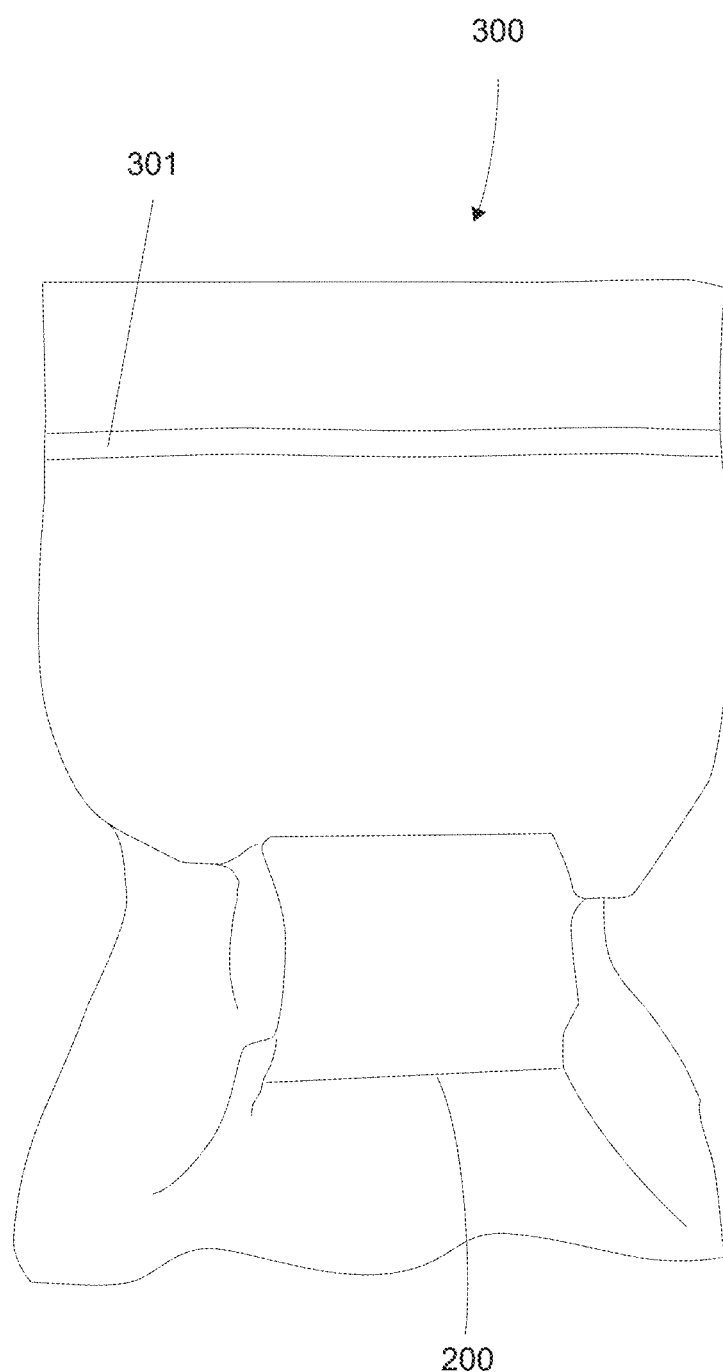
FIG. 3 is a view of the evacuated blood collection container means inserted into a first vacuum sealed container means inserted into a second vacuum sealed container means according to the present invention.

FIG. 3 is a side view of a vacuum-sealed second container means 300 being substantially vacuum-durable, said second container means comprising a first container means 200 further comprising a blood collection container prepared with a high vacuum.

The three containers taken together, i.e. the blood collection container, the first container means 200, and the second container means 300, make up a blood collection kit of parts prepared for transportation, storage and handling.

Preferably, a first container means 200 vacuum-sealed and comprising a blood collection container is sterilised, whereupon it is inserted into a second container means 300, said second container means then being emptied of air thus ensuring that it encloses said first container means tightly, whereupon said second container means is vacuum-sealed thus lowering the pressure differential over the enclosed vacuum barriers and improving the effective vacuum durability of said blood collection container. In one embodiment, when a convenient vacuum has been achieved inside the second container means such as a high vacuum, it is heat sealed at the sealing line 301.

Figure 4:
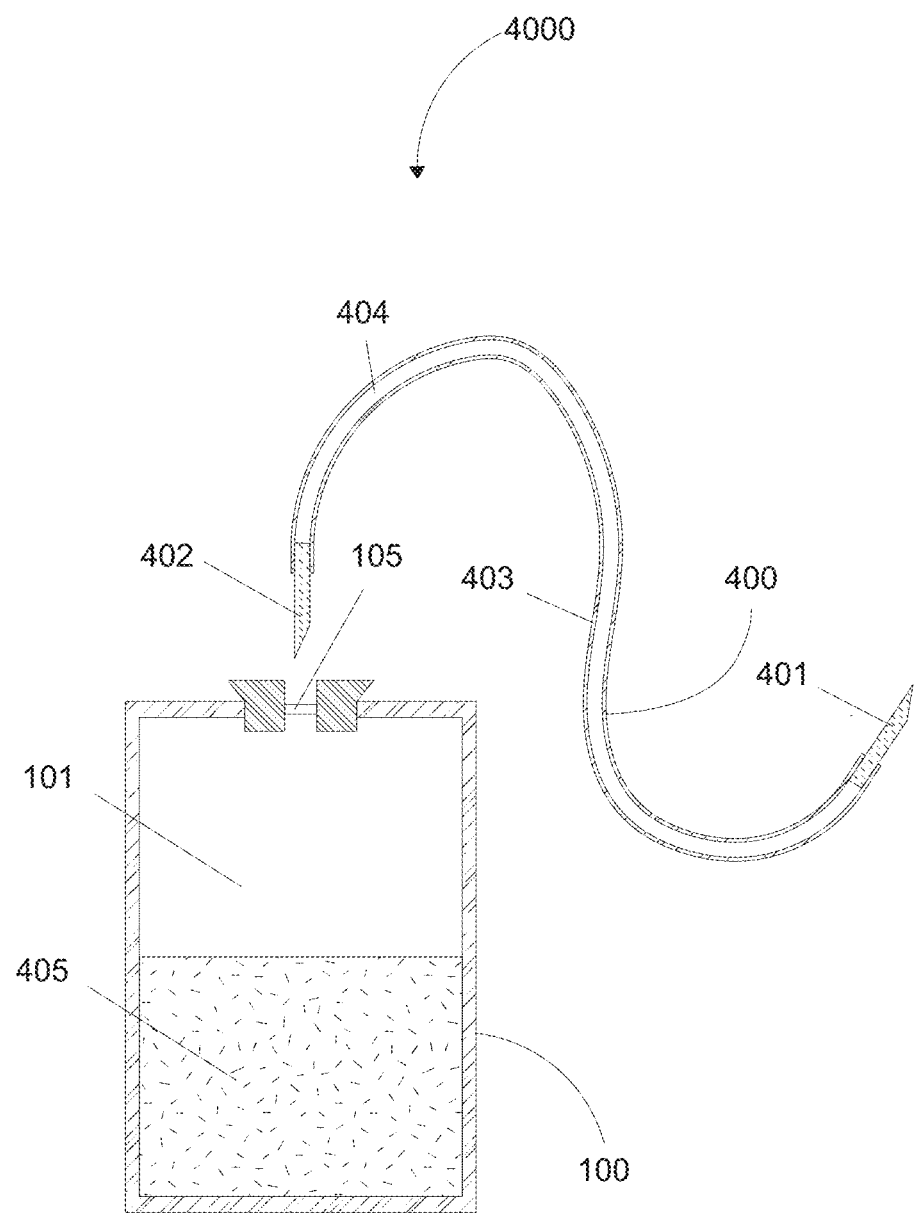
FIG. 4 is a side view of the blood collection container means while drawing blood through a double-ended needle.

FIG. 4 is a side view of a blood collection kit of parts 4000, the kit of parts comprising a blood collection container 100 and a double-ended needle 400 after drawing blood from a patient and disassembling the kit of parts for further processing of the blood.

The blood collection container 100 comprises a bottom wall 102, a side wall 103 defining a container with an open and a closed end, and a stopper in said open end, said stopper further comprising a puncturable septum 105 or a valve for emptying the enclosed inner volume 101 of air thus creating a high vacuum, said puncturable septum or valve further allowing drawing blood into the blood collection container without simultaneously allowing atmospheric air into the inner volume 101. The blood collection container further comprises a blood sample 405.

The double-ended needle comprises a first needle end 401, a second needle end 402, an intermediate tube 403, and an inner volume 404 running the axial length of said double-ended needle, the inner volume allowing the transport of blood from the patient to the blood collection container. In one embodiment of the invention, the inner volume further comprises coagulation accelerating objects, such as one or more glass beads.

In another embodiment of the invention, the double-ended needle further comprises a membrane or pressure valve controlling the flow of blood after injecting the first needle end into a blood-filled cavity such as the vein of a patient and prior to inserting the second needle-end into the blood collection container.

In one embodiment of the invention, the blood collection kit of parts further comprises a first container means 200 and a second container means 300.

A high vacuum may be introduced into the blood collection container by any convenient method. Preferably a blood collection kit of parts 4000 is unpackaged thus allowing access to the blood collection container 100 from within a first and a second container means, the blood collection container being previously prepared with a high vacuum. Then the first needle head 401 enters a convenient volume of the patient, typically a vein, whereupon blood begins running through the inner volume 404 of the double ended needle and simultaneously blocking fluid communication from the blood collection container to outside ambient pressure through the double-ended needle at the first needle end 401. In another embodiment, a membrane or pressure valve at a convenient location inside the double-ended needle, preferably close to the second needle-end, blocks the flow of blood prior to bringing the two inner volumes 101, 404 into fluid communication. This allows easier handling by not needing as careful handling and observation to ensure the blood does not run out of the second needle end prior to puncturing the self-sealing septum as well as a controlled and limited depressurisation as consequence of bringing the two inner volumes into fluid communication since the blood will have pushed a certain controlled, preferably high amount of the air out of the double-ended needle. For example, this membrane or valve comprises rubber or another convenient material. Bringing the inner volumes into fluid communication breaks or opens the membrane or opens the valve and allows the blood to flow.

In the case of using a double-ended needle with a membrane, valve or without either, a second needle end 402 then punctures the self-sealing septum of a blood collection container 100 which brings the high vacuum inner volume of the blood collection container 101 into fluid communication with the inner volume of the double-ended needle 404, this fluid communication decreasing the pressure in the inner volume of the double-ended needle 404 and so actuates an accelerated blood draw.

Figure 5:
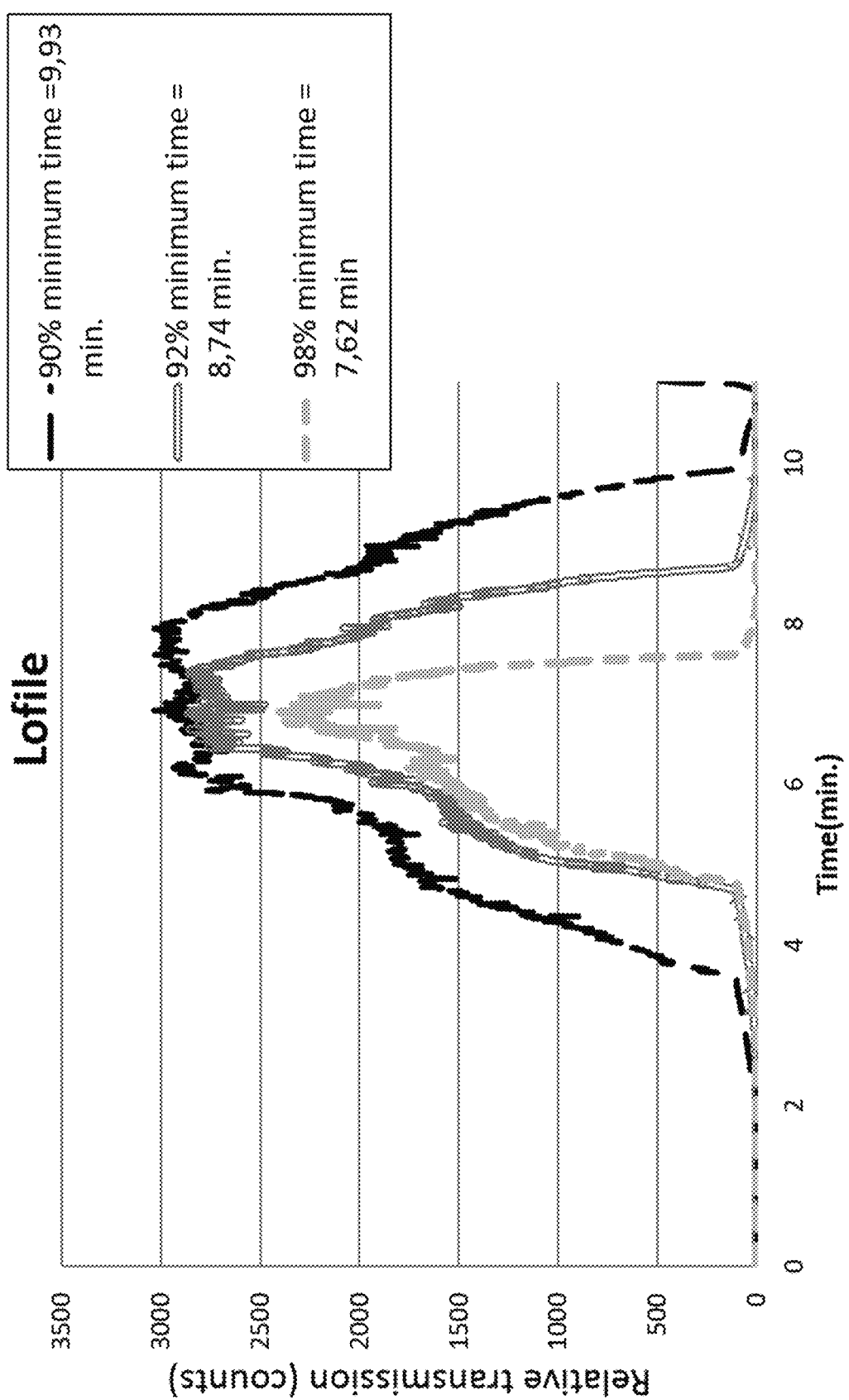
FIG. 5 details measurement data demonstrating the effects of degrees of vacuum on coagulation of blood.

FIG. 5 is measurement data of the various effects on coagulation speed by using 90% (101 mBar), 92% (81 mBar) and 98% (20 mBar) vacuum in a blood collection container during blood filling, Thereafter inserted into a centrifuge, where the coagulation process is observed by way of the translucency of the top part of the blood sample.

In a first phase, translucency increases continually as the blood separates and blood plasma remains in the uppermost part due to it comprising elements relative to the rest of the blood lower Svedberg values, which means forces like gravity, and the centripetal force acts less strongly on these elements and may be thought of as an alternative property to mass for the sake of this invention.

In a second phase, fibrin in the blood plasma begins polymerising thus reducing translucency as the blood plasma becomes more opaque. This reduces transmission counts. Table 1 describes the events shown in FIG. 5:

TABLE 1

|  | 90% | 92% | 98% |
|---|---|---|---|
| peak transmission count at | 7.94 minutes | 7.45 minutes | 6.91 minutes |
| post-peak lowest transmission count at | 9.93 minutes | 8.74 minutes | 7.62 minutes |

Figure 6:
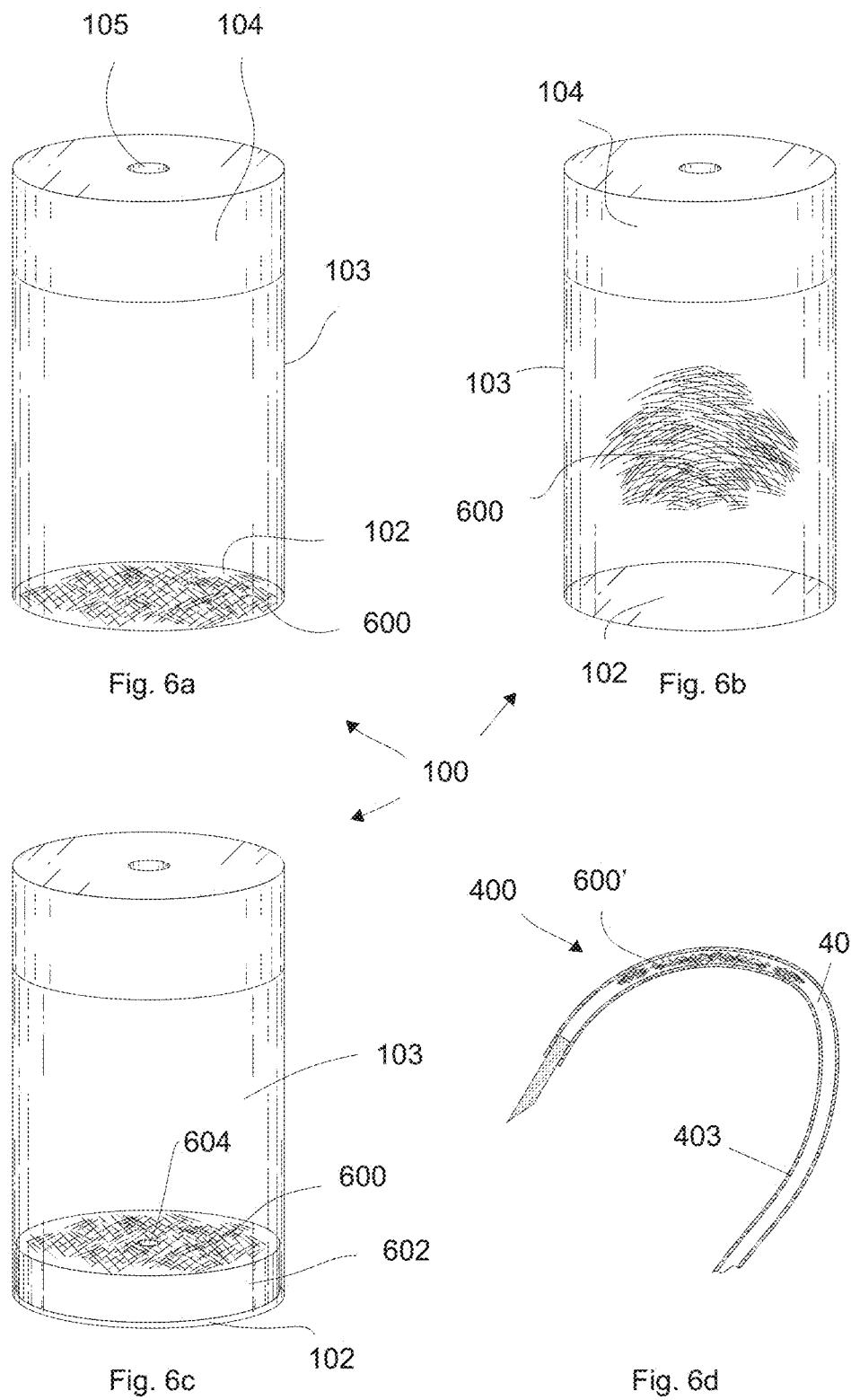
FIG. 6 illustrates various blood coagulation containers with roughened inside surfaces.

FIG. 6 illustrates various embodiments of the invention. All embodiments shown in FIG. 6 illustrate a blood collection container as previously described with a bottom wall 102, an open end with a stopper 104, and a sidewall spanning between 103. The stopper has a self-sealing septum 105.

The inside surface of the blood collection container 100 is provided with an activation site 600. In FIG. 6a, the bottom surface is provided with an activation site 600. The activation site has a high roughness average (Ra) which has been found to increase coagulation speed significantly. By providing the activation site 110 at the bottom of the blood collection container 100, the blood will be pressed against it during centrifugation thus enhancing the effect hereof.

FIG. 6b illustrates an embodiment, where the activation site 600 is provided on the sidewall. The embodiments shown in FIGS. 6a and 6b may be combined to provide more activation sites and/or spreading these around in the blood collection container 100.

FIG. 6c illustrates an embodiment of the invention, where the activation site 600 is provided in an insert 602. The illustrated insert is a float which has an inner volume with a lower density than blood thus allowing lifting the float during or after centrifugation. Thereby, as the blood travels through the central hole 604 to beneath the float 602 during lifting the float 602, the blood will move over the activation site 600 on the insert 602 and thus expose more blood to the activation site 602. There may be provided any kind of channels through or next to the insert in accordance with the invention.

FIG. 6d illustrates a double-ended needle 400 mostly as previously described. The double-ended needle 400 has on its inner surface 406 an activation site 600' that is an area with a high roughness. As the blood passes the activation site 600', the coagulation cascade is initiated. This allows early and thorough coagulation activation.

Generally, the inner surface of the collection unit being the double-ended needle or the container should at least partly have a surface with a high roughness (activation site), whereby the surface is non-smooth, and where this non-smooth surface influences the coagulation speed. As mentioned above, the non-smooth surface could be provided on the sidewalls or bottom walls of the container itself or it could be provided on inserts positioned in the container.

The inner surface of a plastic container could e.g. be made non-smooth to increase the roughness by abrading the surface e.g. using abrading machinery or manually using abrading material.

Figure 7:
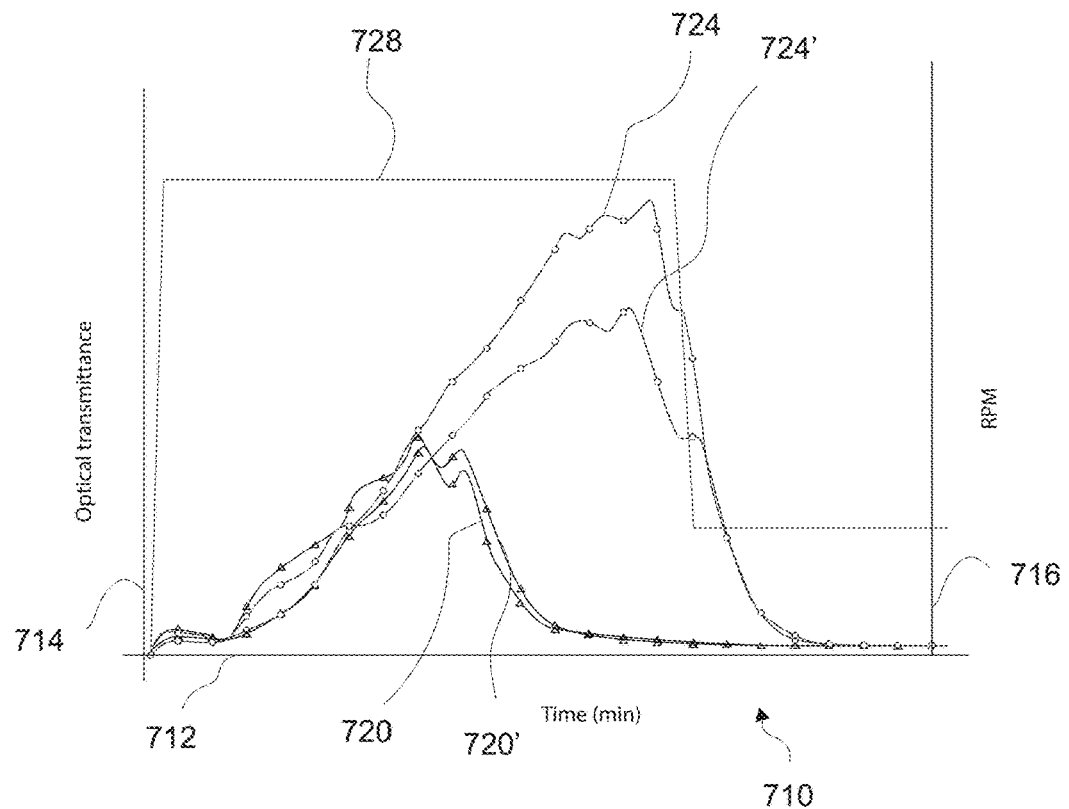
FIG. 7 illustrates readings during a controlled experiment of a rough inside surface.

FIG. 7 shows a controlled experiment of the effect of a rough surface on blood coagulation 710, even when the surface is of a hydrophobic material. The experiment measured optical transmittance 714 and RPM of the centrifuge 716 as functions of time 712.

The experiment was conducted on two identical samples. One was exposed to a rough inside surface, the test sample 720, 720' and the other were not exposed to a rough inside surface, i.e. the control sample 724, 724. Centrifuge work speed 728 was also measured. The variance between 720 and 724 on the one side and 720' and 724' on the other side is due to two sensor locations of the container during centrifugation.

The optical transmittance 714 changes during the experiment as a result of the coagulation. At first, when the blood is still mixed and in liquid form, the optical transmittance is low as light cannot penetrate the blood. During centrifugation, the blood is separated into several layers—at first a plasma layer at the top being yellowish transparent, a buffy coat layer being a more opaque white in the middle, and a dark red layer of erythrocytes (red blood cells) at the bottom. These layers emerge as the heavier molecules are drawn to the bottom of the blood collection container. Subsequently, fibrin gradually polymerises from the plasma layer and descends onto the buffy coat layer. Without the fibrin, the top layer is then serum which is even more transparent than plasma. The polymerised fibrin is an opaque yellowish white.

The optical transmittance 714 is measured at the top of the container in what becomes the plasma fraction during centrifugation. Therefore, the optical transmittance increases steadily as heavy and generally light-absorbing molecules descend. This is initially comparative between the test sample 720 and the control sample 724. However, the translucency drops off for the test sample 720 earlier than for the control sample 724 thus indicating that fibrin is polymerising significantly earlier due to the rough surface.

Figure 8:
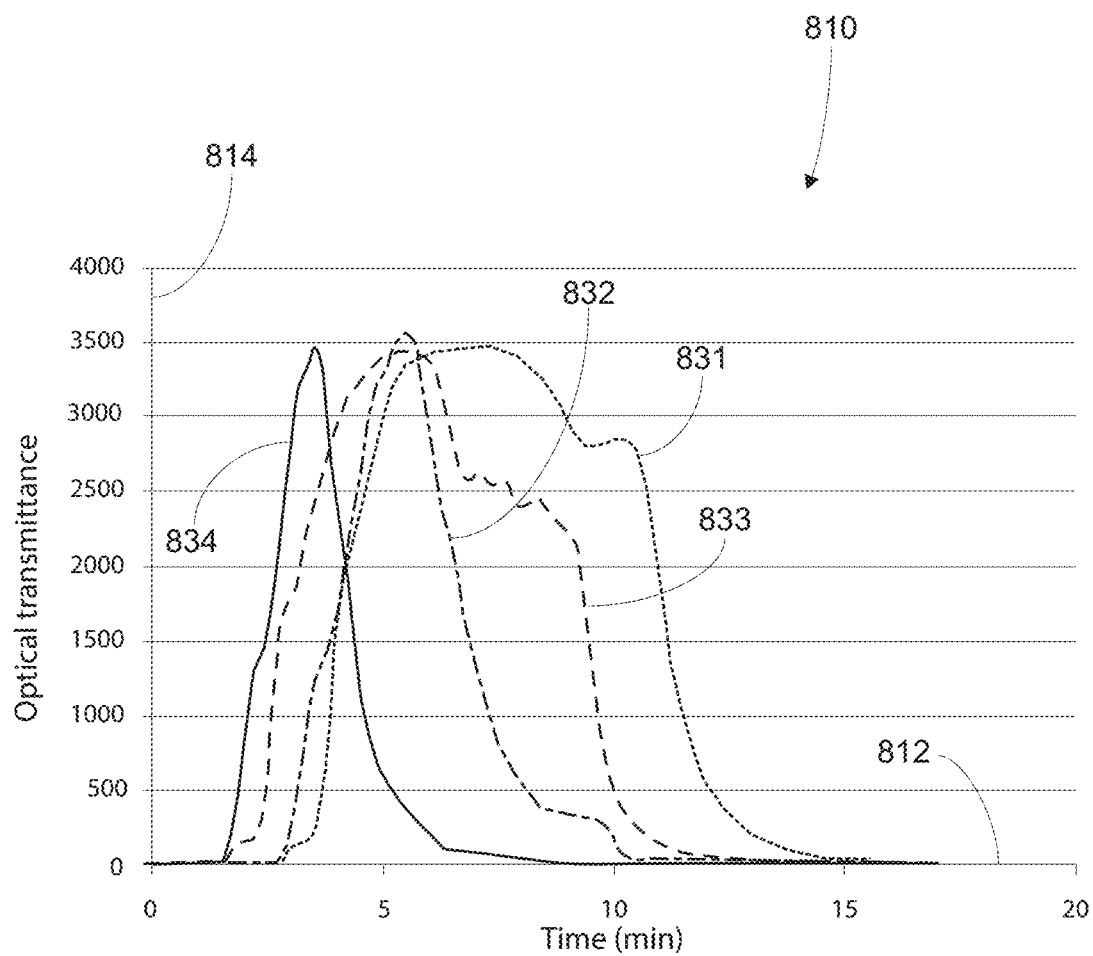
FIG. 8 illustrates the effect of combining high vacuum and rough surface.

FIG. 8 shows a controlled experiment of the effect of combining a high vacuum with a rough surface on blood coagulation 810. The experiment measured optical transmittance 814 as function of time 812. The blood considered has been exposed to centrifugation during the time considered. Thus, the optical transmittance 814 changes during the experiment as a result of the coagulation taking place during centrifugation. The process of coagulation and its impact on optical transmittance 814 is identical to the one described in FIG. 7.

The experiment of FIG. 8 was conducted on four identical whole blood samples. The samples were drawn into four different blood collection containers all comprising different environments: The first sample 831 was exposed to a vacuum of 80% (202.65 mBar), the second sample 832 was exposed to a vacuum of 98% (20.27 mBar), the third sample 833 was exposed to a vacuum of 80% (202.65 mBar) and a surface comprising an activation site having a high roughness, and the fourth sample 834 was exposed to a vacuum of 98% (20.27 mBar) and a surface comprising an activation site having a high roughness.

Considering first the samples exposed to vacuum only, the optical transmittance 814 of both the first 831 and the second 832 samples are seen to increase steadily and comparatively. However, the optical transmittance 814 drops off for the second sample 832 earlier than the first sample 831 thus indicating that fibrin is polymerising, i.e. coagulation is taking place significantly earlier in the high vacuum of the second sample 832 than for the first sample 831 comprising a relatively lower vacuum.

Considering the third 833 and the fourth 834 sample, both being exposed to an activation site having a high roughness, the optical transmittance 814 is seen to increase steadily and comparatively at first. However, it is seen that the fourth sample 834, which is further exposed to a relatively higher vacuum (98%, 20.27 mBar) than the third sample 833, drops off earlier than said third sample which is exposed to a relatively lower vacuum (80%, 202.65 mBar) than the fourth sample 834. Furthermore, it is seen that the fourth sample 834 coagulates earlier than the second sample 832 despite both being exposed to the same vacuum. The same is seen for the third sample 833 coagulating earlier than the first sample 831.

Thus, from the experiment 810, it is seen partly that a high vacuum causes faster coagulation of blood than a relatively lower vacuum and partly that a surface comprising an activation site having a high roughness causes coagulation faster than a surface not comprising such activation site. Most importantly, it is further seen that the combination of a high vacuum (98%, 20.27 mBar) and a surface comprising an activation site having a high roughness (i.e. the fourth sample 834) causes coagulation of blood before any other combinations (the first 831, the second 832, and the third 833 sample).

High Vacuum=A pressure of no more than 255 mBar, 253.31 mBar, 202.65 mBar, 151.99 mBar, 101.33 mBar, 91.19 mBar, 81.06 mBar, 70.93 mBar, 60.80 mBar, 50.66 mBar, 40.53 mBar, 30.40 mBar, 20.27 mBar, 10.13 mBar, 5.07 mBar, 1.01 mBar, 0.10 mBar or less, and where the preferable range of pressure is 0.10 mBar-101.33 mBar or less.

In another embodiment of the invention, said high vacuum corresponds to a vacuum of at least 75% (253.31 mBar), 76% (243.18 mBar), 77% (233.05 mBar), 78% (222.92 mBar), 79% (212.78 mBar), 80% (202.65 mBar), 81% (192.52 mBar), 82% (182.39 mBar), 83% (172.25 mBar), 84% (162.12 mBar), 85% (151.99 mBar), 86% (141.86 mBar), 87% (131.72 mBar), 88% (121.59 mBar), 89% (111.46 mBar), 90% (101.33 mBar), 91% (91.19 mBar), 92% (81.06 mBar), 93% (70.93 mBar), 94% (60.80 mBar), 95% (50.66 mBar), 96% (40.53 mBar), 97% (30.40 mBar), 98% (20.27 mBar), 99% (10.13 mBar), 99.5% (5.07 mBar), 99.9% (1.01 mBar), 99.99% (0.10 mBar) or above as measured linearly, where 0% vacuum is 1013.25 mBar and 100% vacuum is 0 mBar, and where the preferable range of vacuum is 90%-99.99% or above.

$V_r$, is a relatively defined inner volume 404 of a double-ended needle 400=1%, 2%, 3%, 4%, 5%, 6%, 7%, 8%, 9%, 10% or less relative to the volume of the blood collection container 100.

$V_a$, is an absolutely defined inner volume of the double-ended needle, where it corresponds to $V_r$ for a blood collection container of 10 ml=0.1 ml being 1% of 10 ml, 0.2 ml, 0.3 ml, 0.4 ml, 0.5 ml, 0.6 ml, 0.7 ml, 0.8 ml, 9 ml or 1.0 ml being 10% of 10 ml. Vacuum Durability=a quality of a boundary enclosing an environment defining its ability to maintain a percentage of a pressure differential over said boundary over time, specifically where there is a pressure drop from the exterior to the enclosed environment. Two distinct degrees of vacuum durability is described; transitory vacuum durability and substantial vacuum durability, where:

A boundary with a transitory vacuum durability maintains at least 10% of its pressure differential over 24 hours, 48 hours, 72 hours, 96 hours, 120 hours, 144 hours, 168 hours or more, where the initial pressure inside the enclosed environment is a high vacuum and relative to 1013.25 mBar at ambient temperature outside.

A boundary with a substantial vacuum durability maintains at least 98% of its pressure differential over 1 week, 2 weeks, 3 weeks, 4 weeks, 6 weeks, 8 weeks, 12 weeks or more, where the initial pressure inside the enclosed environment is a high vacuum and relative to 1013.25 mBar at ambient temperature outside.

Blood collection container=a container specifically designed for storage and collection of blood immediately after drawing blood from a patient. Such blood collection containers may be used in subsequent treatment of the blood such as in producing LeucoPatch®, or it may only be used for transportation and storage of the blood for later use. Blood collection containers are most conveniently produced in glass, polyethylene terephthalate (PET) and/or polystyrene (PS).

Double-ended needle=typically a tube with a needle in both ends, preferably being able to puncture skin and a vein in the one end and a puncturable septum in the other end. In other embodiments of the invention, the double-ended needle may be regarded as any tube the ends of which are injected into an upstream blood-filled cavity, such as a vein or a blood container, and a downstream blood collection container despite the ends not being actual needles, the term double-ended needle encompassing catheters and tubes as well. Double-ended needles are conveniently produced in silicone, polyurethane, polyethylene and/or Teflon/PFTE.

A. A blood collection container (100) having a bottom wall (102) and a side wall (103) defining an open end, a stopper (104) in said open end, said stopper (104) further comprising a puncturable self-sealing septum (105) or valve, said elements defining an interior volume (101) of said blood collection container (100), characterised in that the interior volume (101) has been prepared with a pressure in its inner volume (101) of no more than 255 mBar.

B. A blood collection container (100) according to embodiment A, wherein said inner volume (101) is prepared with a pressure of no more than 200 mBar.

C. A blood collection container (100) according to any of embodiments A-B, wherein said inner volume (101) is prepared with a pressure of no more than 130 mBar.

D. A blood collection container (100) according to any of embodiments A-C capable of retaining at least 10% of the pressure differential between the high vacuum in its inner volume (101) relative to ambient temperature and pressure on the outside after 24 hours.

E. A blood collection container (100) according to any of embodiments A-D further comprising components adapted to counteract anti-coagulants added to the blood, such as calcium, inside the blood collection container (100).
F. A blood collection container (100) according to any of embodiments A-E, where at least part of the inner surfaces (106, 107, 108) of said blood collection container (100) surrounding the inner volume (101) are corona-treated.
G. A blood collection container (100) according to any of embodiments A-F further comprising a blood coagulation acceleration agent inside the blood collection container (100).
H. A blood collection container (100) according to any of embodiments A-G further comprising an activation site (600) formed in the inside surface (106, 107, 108), the activation site having a high roughness.
I. A blood collection container (100) according to embodiment H, where the activation site (600) has a roughness of at least 0.012 μm.
J. A blood collection container (100) according to any of embodiments H-I, where said activation site is hydrophobic.
K. A blood collection container (100) according to any of embodiments H-J, where the inside surface (106, 107, 108) is hydrophobic.
L. A blood collection container (100) according to any of embodiments H-K made of a hydrophobic material.
M. A blood collection kit of parts (4000) comprising a blood collection container (100) for accelerated coagulation of blood according to any of embodiments A-L, wherein said kit of parts further comprises a first container means (200) and a second container means (300), said second container means (300) being capable of retaining at least 98% of the pressure differential between the vacuum in its inner volume relative to ambient temperature and pressure on the outside after one week, the second container means (300) vacuum being sealed around said first container means (200) which is capable of retaining at least 10% of the pressure differential over its enclosing walls after 24 hours, the first container means (200) being vacuum-sealed around said blood collection container (100).
N. A blood collection kit of parts (4000) according to embodiment M, where the first container means (200) comprises PS and/or PET and the second container means (300) comprises aluminium or aluminium foil.
O. A blood collection kit of parts (4000) comprising a blood collection container (100) for accelerated coagulation of blood according to any of embodiments A-N further comprising a double-ended needle (400) comprising a first needle end (401), a second needle end (402), an intermediate tube (403), and an inner volume (404) running the axial length of said double-ended needle (400), where the combination of the degree of vacuum prepared in said inner volume of the blood collection container (101) and said inner volume of said double-ended needle (404) is such that bringing the two inner volumes (101, 404) into fluid communication retains a pressure of no more than 255 mBar, preferably no more than 200 mBar, even more preferably no more than 130 mBar inside the combined inner volumes (101, 404).
P. A blood collection kit of parts (4000) according to embodiment O, wherein said double-ended needle (400) further has a procoagulant environment (404).

A blood collection kit of parts (4000) according to embodiment P, wherein said procoagulant environment comprises an activation site (600') on an inner surface (406) of said double-ended needle (400) having a high roughness.

The invention claimed is:
1. A blood collection unit for coagulating whole blood for subsequent autologous or allogeneic use, comprising:
an outer wall comprising a closed bottom end, an open top end, a side wall spanning between the ends to form an inside surface, and a stopper inserted into the open top end to releasably seal the blood collection unit, the stopper having a puncturable self-sealing septum or valve;
an inner volume of the blood collection unit defined within the outer wall between the closed bottom end and the stopper,
wherein the inner volume is pressurized at a coagulation accelerating vacuum of at least 90% so that coagulation of blood in the blood collection unit is accelerated;
a coagulation activation site disposed in the inner volume of the blood collection unit and that has an uncoated surface with a roughness, RRMS, of at least 0.012 μm, and
an insertable insert disposed in the inner volume of the blood collection unit,
wherein the coagulation activation site is formed on the insertable insert.
2. The blood collection unit according to claim 1, wherein the roughness, RRMS, is at least 0.4 μm.
3. The blood collection unit according to claim 1, wherein the coagulation activation site is hydrophobic.
4. The blood collection unit according to claim 1, wherein the inside surface is hydrophobic.
5. The blood collection unit according to claim 1, wherein the blood collection unit is made of a hydrophobic material.
6. The blood collection unit according to claim 1, wherein the inner volume is at an absolute pressure of no more than 100 mBar.
7. The blood collection unit according to claim 1, wherein the inner volume is at an absolute pressure of no more than 81.06 mBar.
8. The blood collection unit according to claim 1, wherein the inner volume is at an absolute pressure of no more than 50.66 mBar.
9. The blood collection unit according to claim 1, wherein the inner volume is at an absolute pressure of no more than 20.27 mBar.
10. The blood collection unit according to claim 1, wherein the coagulation activation site is disposed on the inside surface of the side wall.
11. The blood collection unit according to claim 1, wherein the coagulation activation site is disposed on the inside surface of the bottom end.
12. The blood collection unit according to claim 11, wherein the coagulation activation site is disposed on the inside surface of the side wall.
13. The blood collection unit according to claim 1, wherein the inside surface has not been corona treated or plasma treated.
14. The blood collection unit according to claim 1, wherein the insertable insert comprises a float that has an inner volume with a lower density than blood so that the float lifts the insertable insert in the blood collection unit during or after centrifugation and a mesh that is configured to collect at least a fibrin fraction of the whole blood during coagulation.

* * * * *